(12) United States Patent
Xu et al.

(10) Patent No.: US 7,965,914 B2
(45) Date of Patent: Jun. 21, 2011

(54) CRITICALLY COUPLED MICRORING RESONATOR AND METHOD

(75) Inventors: Qianfan Xu, Houston, TX (US); David A. Fattal, Mountain View, CA (US); Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 315 days.

(21) Appl. No.: 12/262,160

(22) Filed: Oct. 30, 2008

(65) Prior Publication Data

US 2010/0110417 A1    May 6, 2010

(51) Int. Cl.
*G02B 6/26* (2006.01)
*G02B 6/12* (2006.01)
*G06F 7/60* (2006.01)

(52) U.S. Cl. .................. 385/50; 385/14; 703/2

(58) Field of Classification Search .................. None
See application file for complete search history.

(56) References Cited

U.S. PATENT DOCUMENTS

| | | | |
|---|---|---|---|
| 6,052,495 A | 4/2000 | Little et al. | |
| 6,885,794 B2 | 4/2005 | Scheuer et al. | |
| 6,907,152 B2 | 6/2005 | Takahashi et al. | |
| 7,123,800 B2 | 10/2006 | Kaplan | |
| 7,424,192 B2 * | 9/2008 | Hochberg et al. | 385/122 |
| 7,536,070 B2 * | 5/2009 | Rosa de Almeida et al. | 385/31 |
| 2006/0062523 A1 | 3/2006 | Guo et al. | |
| 2006/0171635 A1 * | 8/2006 | Lee et al. | 385/50 |

OTHER PUBLICATIONS

S. C. Hagness et al.,"FDTD Microcavity Simulations: Design and Experimental Realization of Waveguide-Coupled Single-Mode Ring and Whispering-Gallery-Mode Disk Resonators," Journal of Lightwave Technology, vol. 15, No. 11, Nov. 1997, pp. 2154-2165.
M. K. Chin et al., "Design and Modeling of Waveguide-Coupled Single-Mode Microring Resonators," Journal of Lightwave Technology, vol. 16, Issue 8, 1998, pp. 1433-1446.
Shijun Xiao et al., "Compact silicon microring resonators with ultra-low propagation loss in the C band," Optics Express, vol. 15, No. 22, Oct. 29, 2007, pp. 14467-14475.
Ye Liu et al., "Coupled mode theory for modeling microring resonators," Optical Engineering, vol. 44, No. 8, Aug. 2005, pp. 084601-1 to 084601-6.
Shengmei Zheng et al., "Microring resonator-coupled waveguide crossings in silicon nitride: waveguide width tuning," Group IV Photonics, 2004. First IEEE International Conference on, Sep. 29-Oct. 1, 2004, pp. 25-27.
Vittorio M. N. Passaro et al.,"Ammonia Optical Sensing by Microring Resonators," Sensors, 2007, vol. 7, pp. 2741-2749.
Donald S. Gardner et al.,"Microring and microdisk optical resonators using silicon nanocrystals and erbium prepared using silicon technology," Optical Materials, vol. 27, 2005, pp. 804-811. (Available online Oct. 18, 2004, www.sciencedirect.com).
Qianfan Xu et al., "Silicon microring resonators with 1.5-μm radius," OPTICS EXPRESS, vol. 16, No. 6, Mar. 14, 2008, pp. 4309-4315.

* cited by examiner

*Primary Examiner* — Omar Rojas (57) ABSTRACT

A microring resonator and methods critically couple a microring waveguide to an adjacent bus waveguide. A method of determining parameters of a critically coupled microring resonator includes modeling a coupled portion of the microring resonator as a U-shaped waveguide spaced apart from a straight waveguide by a gap and selecting a straight waveguide width and a gap size to optimize an output coupling ratio between the U-shaped waveguide and the straight waveguide. A method of producing the microring resonator includes using the determined parameters to produce, and a critically coupled microring resonator includes, a ring-shaped or microring waveguide spaced from the bus waveguide by a gap.

20 Claims, 2 Drawing Sheets

CRITICALLY COUPLED MICRORING RESONATOR AND METHOD

CROSS-REFERENCE TO RELATED APPLICATIONS

N/A

STATEMENT REGARDING FEDERALLY SPONSORED RESEARCH OR DEVELOPMENT

N/A

BACKGROUND

1. Technical Field

The invention relates to photonic devices. In particular, the invention relates to optical microring resonators.

2. Description of Related Art

Microring resonators are becoming popular components for use in many modern photonic devices. For example, a silicon microring may provide a CMOS-compatible means for implementing an optical filter, an electro-optical modulator, a laser, and even a detector (although some of these implementations may require that one or more of carrier injection, optical gain or optical absorption mechanisms be incorporated into the microring resonator). The popularity of microring resonators is due in large part to their relatively small size, potentially high quality factor (Q), transparency to off-resonance light, and near lack of intrinsic reflection. While microring resonators, which provide the functionality of a ring resonator in a much more compact size, may lead to many beneficial characteristics (e.g., higher integration density and wide free spectral range), microring resonators that are both critically coupled and that provide sufficiently high Q have proved relatively difficult to achieve in practice. Such a microring resonator would satisfy a long felt need.

BRIEF SUMMARY

In some embodiments of the present invention, a method of determining parameters of a critically coupled optical microring resonator is provided. The method of determining parameters comprises modeling a coupled portion of the microring resonator as a U-shaped waveguide spaced apart from a straight waveguide by a gap. The U-shaped waveguide has a width that is equivalent to a width of a waveguide of the microring resonator. The method of determining parameters further comprises selecting a width of the straight waveguide and a size of the gap to optimize an output coupling ratio between the U-shaped waveguide and the straight waveguide. The selected straight waveguide width and the selected gap size are the determined parameters of the critically coupled optical microring resonator.

In other embodiments of the present invention, a method of producing a microring resonator is provided. The method of producing comprises providing a U-shaped waveguide. The method of producing further comprises providing a straight waveguide segment adjacent to the U-shaped waveguide. The straight waveguide segment is spaced apart from the U-shaped waveguide by a gap. The method of producing further comprises determining a value of a width of the straight waveguide segment and a size of the gap that produces a target output coupling ratio. The method of producing further comprises producing a microring resonator that comprises a ring-shaped waveguide adjacent to a bus waveguide using the determined value of the straight waveguide segment width as a width of the bus waveguide and using the determined gap size as a spacing between the ring-shaped waveguide and the bus waveguide. A width of the ring-shaped waveguide is determined by a width of the U-shaped waveguide.

In yet other embodiments of the present invention, a critically coupled optical microring resonator is provided. The critically coupled optical microring resonator comprises a microring waveguide having a radius that is less than about 2 microns. The critically coupled optical microring resonator further comprises a straight waveguide adjacent to but spaced apart from the microring waveguide. The straight waveguide has a width and is spaced apart from the microring waveguide by a gap. A ratio of a width of the microring waveguide to the straight waveguide width is less than about 0.7 and a ratio of a size of the gap to the microring waveguide width is greater than about 0.5.

Certain embodiments of the present invention have other features that are one of in addition to and in lieu of the features described hereinabove. These and other features of the invention are detailed below with reference to the following drawings.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which.

DETAILED DESCRIPTION

Embodiments of the present invention facilitate realizing an ultra-compact, optical microring resonator. The optical microring resonator (hereinafter referred to as a 'microring resonator') embodiments are critically coupled to a bus waveguide while simultaneously exhibiting relatively high coupled quality factor (i.e., high coupled Q) according to the invention. For example, a critically coupled silicon microring resonator having a radius of about 1.5 microns ($\mu m$) and an effective mode volume of approximately 1.0 $\mu m^3$ with a coupled Q of up to 9,000 may be realized. Moreover, the microring resonator having an overall size that is less than an operational wavelength and that may approach a theoretical size limit may be realized while still providing the high coupled Q, according to embodiments of the present invention. Applications of high Q, critically coupled microring resonators such as those provided by various embodiments of the present invention include, but are not limited to, laser, photonic filters, photonic modulators, and various related photonic and optoelectronic components.

In various embodiments of the present invention, a coupling or junction formed between the microring resonator and the bus waveguide employs a combination of the bus waveguide having a reduced or narrowed width and an increased spacing or gap size between the microring resonator and the bus waveguide when compared to conventional realizations, for example. Selection or determination of a specific value of each of the reduced width and the increased gap size may be made through an optimization, according to some embodiments of the present invention.

In particular, microring resonators typically comprise a tightly bent waveguide (e.g., strip waveguide or ridge waveguide) that is formed into a closed or ring-shape loop. The tightly bent waveguide produces a leaky optical mode within the microring resonator. As a result, an intrinsic or unloaded Q of the microring resonator is inversely proportional to its radius. The smaller the microring resonator, the lower the unloaded Q that may be achieved.

Furthermore, coupling to and from the microring resonator, as is generally necessary for realizing a practical photonic device using the microring resonator, further exacerbates the situation. Coupling to the microring resonator often involves using a segment (e.g., a straight segment) of a so-called 'bus waveguide' that is positioned adjacent to but spaced apart from the microring resonator waveguide. Optical modes in the microring resonator and in the adjacent straight segment of bus waveguide are mismatched due to the tight bend radius of the microring resonator. The mismatch results in optical scattering by the coupling or junction region of the coupled microring resonator which manifests as optical loss.

In conventional realizations, a gap spacing between the straight waveguide segment and the coupled microring resonator usually must be made very small (e.g.,~100μm) to facilitate achieving acceptably high coupling values. The very small gap is both difficult to reliably manufacture and further exacerbates the problem of achieving high coupled Q values with the microring resonator. Specifically, the mismatch of optical modes in the microring resonator and the bus waveguide segment produces a further reduction of the Q (i.e., loaded Q) of the microring resonator due to interference between the optical modes. The interference-based reduction in the loaded Q may be made even worse by the requirement for a small gap spacing of the conventional microring resonator realizations.

According to embodiments of the present invention, the selected or determined reduced width of the bus waveguide may facilitate an improved phase matching between optical modes in the microring resonator and the bus waveguide. For example, narrowing the width of the bus waveguide lowers an effective index of the bus waveguide, which in turn, leads to a longer spatial period of optical modes in the bus waveguide. The longer spatial periods better match or align with optical modes in the curved microring resonator. The matching of the optical mode may reduce a scattering or radiative loss by the junction.

In addition, reducing the width of the bus waveguide also increases a portion of the optical mode of the bus waveguide that extends beyond a guiding portion and into the gap between the microring resonator and the bus waveguide. As such, there is a higher mode overlap between the optical mode of the bus waveguide and the optical mode in the microring resonator. The higher mode overlap increases a coupling between the bus waveguide and the microring resonator, which allows the gap size to be increased for a given desired coupling amount. Such a resultant larger gap size is easier to fabricate. Moreover, a larger spacing between the bus waveguide and the microring resonator represented by the resultant larger gap size may reduce an interfering effect of the bus waveguide on the optical mode in the microring resonator. Both the easier fabrication and reduced interference effect further facilitate a high loaded or coupled Q. Thus, the combination of reduced width and increased gap size may minimize spurious light scattering at and by the junction, which facilitates critical coupling while allowing the relatively high coupled Q to be achieved, according to embodiments of the present invention.

In some embodiments, the microring resonator and the bus waveguide as well as the junction therebetween are realized by employing modeling. In particular, a model of a waveguide of the microring resonator and an adjacent segment of waveguide representing the bus waveguide is constructed. In some embodiments, the model is an actual or physical model and in other embodiments the model may be a virtual or computer model. In either case, various widths of the waveguide segment and sizes of a gap between the microring waveguide and the adjacent waveguide segment are employed in the model. An optimization of a performance of the model is performed using different widths and gap sizes. The optimization produces a best or 'optimum' set of the width and the gap size that then may be used to realize (e.g., construct) the microring resonator and bus waveguide according to some embodiments of the present invention.

According to some embodiments, the microring resonator and its junction are modeled as only a portion of the microring resonator and a similar portion of the adjacent waveguide segment in a vicinity of the junction. In some of these embodiments, the microring resonator is modeled as a U-shaped waveguide. In some embodiments, the U-shaped waveguide comprises a curved portion generally oriented toward the adjacent waveguide segment to provide the junction and a pair of ends generally oriented away from the junction. In some embodiments, the U-shaped waveguide comprises a truncated circular segment of optical waveguide. The truncated circular segment of optical waveguide may be a portion of the microring resonator being modeled. In some embodiments, the U-shaped waveguide further comprises a pair of straight segments of optical waveguide. The straight segments of the pair are connected to the ends of the truncated circular waveguide in the model, according to these embodiments. The individual straight waveguide segments may provide one or both of means for terminating the U-shaped waveguide and a location for introducing an excitation signal. The combination of the U-shaped waveguide adjacent to but spaced apart from the adjacent waveguide segment effectively models both a coupling between the microring resonator and the waveguide segment and scattering and back-reflection losses in the waveguide segment.

In other embodiments, the U-shaped waveguide comprises only the truncated circular segment of optical waveguide. In such embodiments, the truncated circular segment of optical waveguide may provide one or both of means for terminating the U-shaped waveguide (e.g., using ends of the truncated circular segment directly) and a location for introducing an excitation signal (e.g., either at the ends or within the truncated circular segment). In yet other embodiments, the U-shaped waveguide may comprise the curved portion (e.g., a truncated circular segment) and one or more additional segments of optical waveguide attached to the pair of ends. The additional segments may be either curved or straight, in various embodiments. As such, the use of term 'U-shaped' may be employed only be for discussion purposes and not by way of limitation, in some embodiments.

In some embodiments, modeling is performed using finite difference time domain (FDTD) analysis. FDTD is an electromagnetic modeling algorithm based on the direct numerical solution of Maxwell's Equations in the differential, time domain form. In FDTD, a model space containing elements being modeled is represented by a large number of discrete regions or cells (i.e., a discretization). Typically two sets of cells defined on an offset grid are employed. One of the sets represents a magnetic component (i.e., H-field) of an electromagnetic field and another represents an electric component (i.e., E-field) of the electromagnetic field in the model space. A leap-frog, time marching technique is then applied to the cells to compute values of the H-fields and E-fields in each of the cells as a function of time using difference equations that represent an approximation of Maxwell's Equations in terms of a discretized model space.

In some embodiments, the discretization is a two dimensional (2D) discretization yielding a 2D FDTD solution referred to herein as '2D FDTD'. In other embodiments, the discretization is a three dimensional (3D) discretization that provides a 3D FDTD solution referred to herein as '3D FDTD'. An example of a 3D FDTD simulation tool that may be employed to perform the 3D FDTD modeling described herein is MEEP (http://ab-initio.mit.edu/wiki/index.hph/Meep), publicly available modeling tool from the Massachusetts Institute of Technology (MIT). Since FDTD analysis (and especially 3D FDTD analysis) is computationally intensive, FDTD analysis is often performed on a supercomputer such as, but not limited to, a supercomputer cluster system in which multiple computation nodes may facilitate simultaneous simulation of different instances of the model being analyzed.

In either 2D FDTD or 3D FDTD, the cells of the discretization generally need to be small enough to accurately represent the H-field and the E-field being simulated. In practice, this means that there are typically at least 6-8 cells per a maximum or highest wavelength in the simulation. In some embodiments, about 20 cells per wavelength are employed. Using 20 cells per wavelength facilitates achieving an accuracy consistent with realizing the microring resonator according to some embodiments of the present invention. Also, simulation results are often displayed graphically with the discrete values of the H-field and the E-field being represented by pixels within the graphical representation. As such, the cells of the FDTD simulation are often referred to as 'pixels'. For example, a reference to '20 pixels per wavelength' is equivalent to '20 cells per wavelength'.

The terms 'pixels' and 'cells' are used interchangeably herein when discussing FDTD simulation and modeling using FDTD. Thus, in some embodiments, the FDTD simulation described herein employs a resolution of greater than about 6 pixels per wavelength in a material having a highest index of refraction or 'highest index material'. Herein, a material having a 'highest index of refraction' means that the material has a highest index of refraction relative to other materials in a vicinity. For example, the highest index of refraction material would be silicon (Si) when considering a silicon strip waveguide surrounded by a cladding layer comprising silicon dioxide ($SiO_2$). In some embodiments, the FDTD simulation employs about 20 pixels per wavelength in the highest index material. For example, if the simulation is of waveguides realized in silicon (e.g., on a silicon on insulator substrate), then the highest index material is silicon. For a wavelength of about 1.55 μm in silicon, the FDTD simulation may employ about 20 pixels per 1.55 μm, for example.

FDTD simulations often employ a boundary layer at an edge of the model space that terminates the model space in a particular way. For example, some boundary layers used with FDTD attempt to simulate an essentially infinite extension of the model space. Such an infinite extension is characterized by no reflections. One such boundary layer is known as a 'perfectly matched layer' (PML). An electromagnetic wave propagating in a model space of FDTD experiences little or no reflection when it encounters a PML.

In some embodiments, the modeling or simulation described herein is performed on a supercomputer cluster system. The supercomputer/cluster system facilitates an optimization by performing multiple simultaneous FDTD simulations with different gap sizes and waveguide widths at multiple frequencies by distributing the FDTD simulations among multiple available nodes on the supercomputer/cluster system. In other embodiments, another supercomputer system is used.

Herein, a 'microring resonator' is defined as an essentially circular closed loop segment of optical waveguide having a radius that is on the order of one to two wavelengths at an operational wavelength. In some embodiments, the radius is smaller than an operational wavelength. The radius of the microring is measured from a center of the microring resonator to a midpoint of the optical waveguide. For example, a microring resonator may have an operational wavelength of 1.55 μm and comprise a microring formed as a circle having a radius of about 1.5 μm measured from a center of the circle. In another example, the microring may be oval and have a radius (e.g., a maximum radius) of about 3 μm for an operational wavelength of 1.55 μm. A 'microring resonator' as defined herein is distinguished from a conventional optical ring resonator (e.g., any optical ring resonator other than a microring) in that conventional optical ring resonators typically have radii greater than about 5-10 wavelengths.

By 'essentially circular' it is meant that the microring resonator has a closed loop of waveguide formed in a shape that resembles a conic section such as, but not limited to, a circle or an ellipse. For example, the essentially circular microring may have an optical waveguide that has the shape of or describes an actual circle. In other instances the essentially circular microring resonator has a closed loop waveguide that merely resembles but is not actually a conic section. For example, the microring resonator may be an oval. In yet another example, the microring resonator may have a shape that is an approximation of a conic section (e.g., a polygon that approximates a circle).

Herein, 'critical coupling' of a microring resonator is an amount of coupling needed to match a loss in the microring resonator. Specifically, as defined herein, a microring resonator is critically coupled to a bus waveguide when a one-pass optical coupling between the microring resonator and the bus waveguide equals a round trip optical loss in the microring resonator. In other words, critical coupling couples just enough power into the microring resonator from the bus waveguide to offset an amount of loss experienced in one trip around the closed loop of the microring resonator.

Also herein, the term 'flux' refers to electromagnetic or optical flux and is equal to an integral of a Poynting vector over a surface representing by a cross section of the optical waveguide. The Poynting vector $\vec{S}$ is defined by equation (1) as $$\vec{S} = \vec{E} \times \vec{H} \quad (1)$$

where $\vec{E}$ is a vector of an electric field (E) component of a optical mode (or equivalently an optical signal) in the optical waveguide, $\vec{H}$ is a vector of a magnetic field (H) component (sometimes called the auxiliary magnetic field) of the optical mode in the optical waveguide, and '×' is a vector cross product. Essentially, flux is measured at a plane and for a surface that perpendicular to an axis of the optical waveguide and represents an amount of optical power per unit area (i.e., watts per meters squared—$W/m^2$) at or crossing that surface.

Thus, flux is a measure of power flow in the optical waveguide as defined and employed herein. Flux may be measured in an actual waveguide (e.g., with a power or flux meter attached to the waveguide) or may be determined from results of a model of the waveguide represented in a computer simulation (e.g., FDTD). Typically, flux measurements in an optical waveguide employ a surface that extends at least a fraction of a wavelength outside the physical extent of the optical waveguide. Employing such a surface insures that optical energy flowing along but just outside the optical waveguide is captured by the flux measurement. In either case, herein the flux will be referred to as being 'measured' unless a distinction is necessary for proper understanding.

Herein, reference to 'optimize' and 'optimization' and related terms generally means to select or determine a result (i.e., specific parameter values) from among a plurality of discrete results where the selected result best achieves some goal. The terms are not meant to limit the scope of the present invention to a global or true optimum result. Similarly, the term 'minimize' means to select a result from among a discrete set of results that represents an essentially minimum result.

For example, a number of FDTD simulations may be performed with different parameter values. The results of the FDTD simulations are then examined relative to a goal or an objective (e.g., a coupling ratio). The set of parameter values that provides the 'best' results compared to the goal are the selected or determined parameter values of the optimization. What qualifies as a 'best' result is situation dependent but may be readily determined. In some embodiments, the optimization may be manual (e.g., the comparison is performed manually). In other embodiments, the optimization is performed automatically using a computerized optimization technique such as, but not limited to, a gradient optimization, a random or Monte Carlo optimization, and a genetic algorithm optimization.

For simplicity herein, no distinction is made between the terms 'optical waveguide' and 'waveguide' since all waveguides referred to herein are essentially optical waveguides. Moreover, no distinction is made between the terms 'optical microring resonator' and 'microring resonator' since all microring resonator referred to herein are essentially optical microring resonators. Further, as used herein, the article 'a' is intended to have its ordinary meaning in the patent arts, namely 'one or more'. For example, 'a layer' generally means one or more layers and as such, 'the layer' means 'the layer(s)' herein. Also, any reference herein to 'top', 'bottom', 'upper', 'lower', 'up', 'down', 'left' or 'right' is not intended to be a limitation herein. Moreover, examples herein are intended to be illustrative only and are presented for discussion purposes and not by way of limitation.

Figure 1:
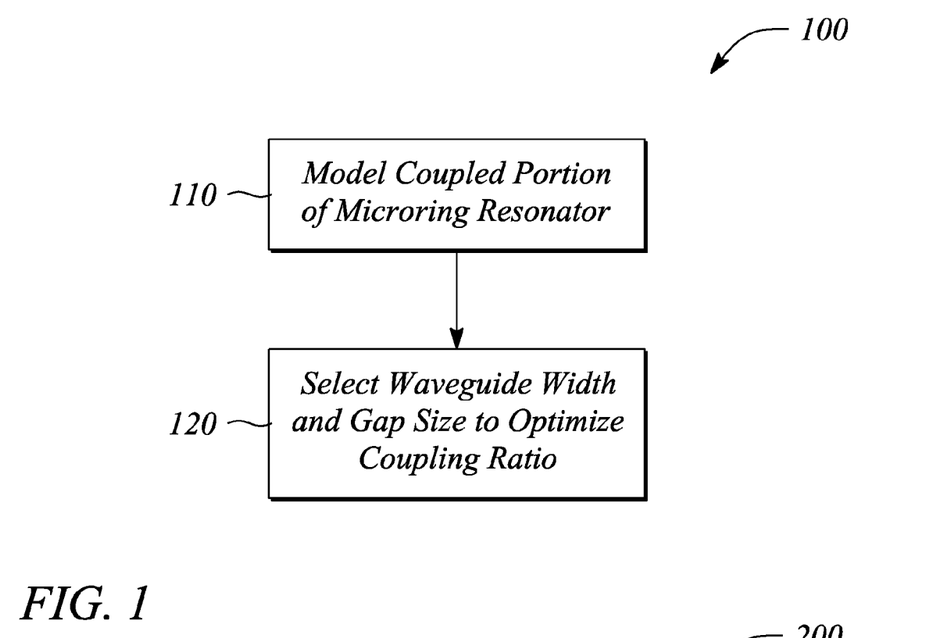
FIG. 1 illustrates a flow chart of a method of determining parameters of a critically coupled optical microring resonator, according to an embodiment of the present invention.

FIG. 1 illustrates a flow chart of a method 100 of determining parameters of a critically coupled optical microring resonator, according to an embodiment of the present invention. In particular, the method 100 determines parameters including a width of a bus waveguide and a size of a gap between a microring resonator and a bus waveguide to which the microring resonator is coupled. The determined parameters may provide critical coupling of the microring resonator.

The method 100 of determining parameters comprises modeling 110 a coupled portion of the microring resonator. The coupled portion is modeled 110 as a U-shaped waveguide spaced apart from a straight waveguide by a gap. The U-shaped waveguide has a width that is equivalent to a width of a waveguide of the microring resonator. Moreover, a radius of the U-shaped waveguide is equivalent to a radius of the microring resonator.

Figure 2:
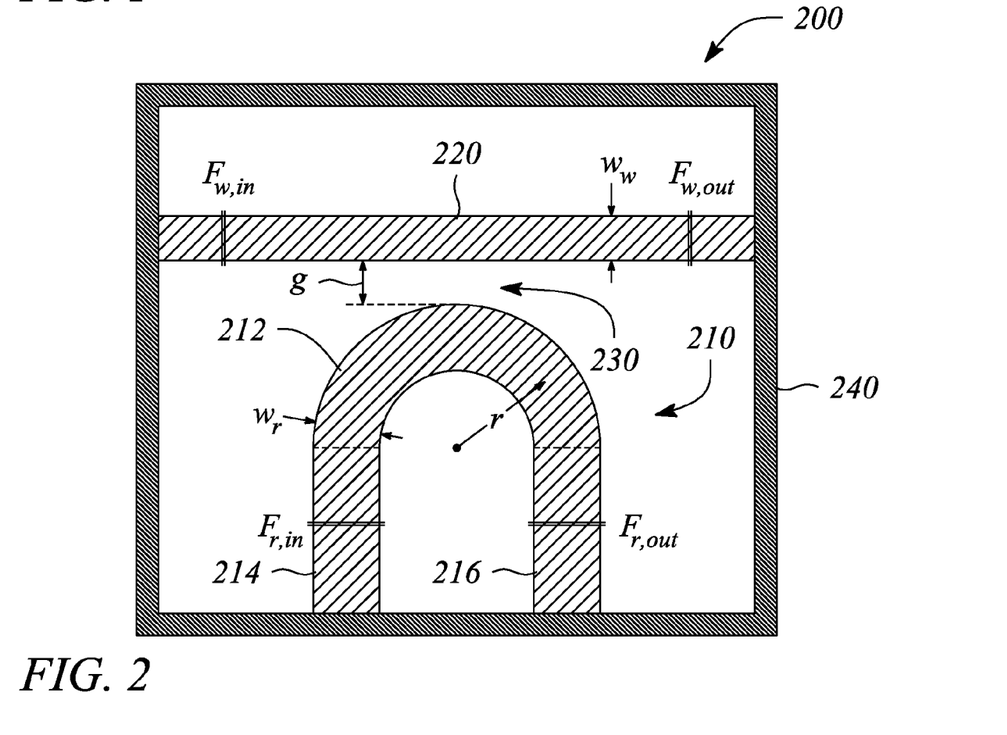
FIG. 2 illustrates a top view of a model of a coupled portion of a microring resonator, according to an embodiment of the present invention.

FIG. 2 illustrates a top view of a model 200 of a coupled portion of a microring resonator, according to an embodiment of the present invention. Illustrated in FIG. 2 are the U-shaped waveguide 210 and the straight waveguide 220 separated by the gap 230. The U-shaped waveguide 210 has a width $w_r$ that is equivalent to a width of a waveguide of the microring resonator being modeled. The U-shaped waveguide 210 comprises a truncated circular portion 212 (e.g., a half circle) and a pair of straight waveguide segments 214, 216. The truncated circular portion 212 has a radius r that is equivalent to a radius of the microring resonator being modeled. A first straight waveguide segment 214 of the pair is connected to a first end of the truncated circular portion 212 while a second straight waveguide segment 216 is connected to a second end of the truncated circular portion 212. The straight waveguide 220 has a width $w_w$. The gap 230 has a gap size g in FIG. 2.

Optical flux measurements and resulting optical flux values referred to below are performed on the model 200 of the coupled portion at four measurement planes representing an input of the straight waveguide 220, an output of the straight waveguide 220, an input of the U-shaped waveguide 210 and an output of the U-shaped waveguide 210. In particular, a first flux measurement $F_{w,in}$ (or equivalently a first flux value) represents an optical flux at the input to the straight waveguide 220. A second flux measurement and value $F_{w,out}$ represents an optical flux at the output of the straight waveguide 220. A third flux measurement and value $F_{r,in}$ represents the optical flux at the input of the U-shaped waveguide 210 while a fourth flux measurement and value $F_{r,out}$ represents the optical flux at the output of the U-shaped waveguide 210. In FIG. 2, measurement planes associated with the four flux measurements/values are labeled $F_{w,in}$, $F_{w,out}$, $F_{r,in}$, and $F_{r,out}$, respectively.

Referring back to FIG. 1, in some embodiments, modeling 110 comprises providing a finite difference time domain (FDTD) simulation (or equivalently FDTD model) of the U-shaped waveguide and straight waveguide. In an FDTD simulation, a model space of the FDTD simulation is terminated by a 'matched' boundary layer. The ends of the U-shaped waveguide and the straight waveguide may also be terminated by the matched boundary layer, in some embodiments. In other embodiments, the ends are terminated in another way (e.g., an absorber element at the ends of the respective waveguides). In some of these embodiments, the provided FDTD simulation is a three dimensional (3D) FDTD simulation and the matched boundary layer is a perfectly matched layer (PML).

In FIG. 2, an exemplary PML 240 is illustrated as a band of cells or pixels that surrounds the model 200. For a 3D FDTD, the band would completely surround the FDTD model space. The exemplary PML 240 provides an essentially reflectionless termination of the model space of the FDTD simulation. The PML 240 also provides a matched or essentially reflectionless termination for the pair of straight waveguide segments 214, 216, and the two ends of the straight waveguide 220. In particular, the PML 240 is used to provide an essentially reflectionless termination of the pair of straight waveguide segments 214, 216, beyond the measurement planes $F_{r,in}$ and $F_{r,out}$, as is illustrated in FIG. 2. Similarly, the PML 240 is used to provide an essentially reflectionless termination of both of the input and the output of the straight waveguide 220 beyond the measurement planes $F_{w,in}$ and $F_{w,out}$, as is further illustrated in FIG. 2.

Referring again to FIG. 1, the method 100 of determining parameters further comprises selecting 120 a width of the straight waveguide and a size of the gap to optimize an output coupling ratio between the U-shaped waveguide and the straight waveguide. In some embodiments, the selected straight waveguide width is less than the U-shaped waveguide width and the selected gap size is greater than the straight waveguide width.

In some embodiments, the output coupling ratio is given by a ratio of an optical flux at the straight waveguide output to an optical flux at the U-shaped waveguide input. The output coupling ratio essentially quantifies an amount or portion of optical flux in the U-shaped waveguide that is coupled to and further reaches the output of the straight waveguide. In some embodiments, the output coupling ratio is determined by introducing an optical signal at the U-shaped waveguide input and measuring both the optical flux at the straight waveguide output and the optical flux within the U-shaped waveguide after the introduction of the optical signal. An appropriate ratio of the measured optical fluxes then yields the output coupling ratio.

Referring to FIG. 2 for example, the output coupling ratio $\kappa_{out}$ may be defined by equation (2) as $$\kappa_{out} = \frac{F_{w,out}}{F_{r,in}} \qquad (2)$$

where $F_{w,out}$ is the optical flux at the straight waveguide 220 output measurement plane and $F_{r,in}$ is the optical flux at the U-shaped waveguide 210 input measurement plane, as described above. Again with reference to FIG. 2, an optical signal may be introduced by providing an optical source to excite an optical flux in the U-shaped waveguide 210. The optical source may be located in the straight segment 214 at a point beyond the input measurement plane $F_{r,in}$, for example. In particular, when an FDTD simulation is employed, the optical source may be located between the input measurement plane $F_{r,in}$ and the PML 240.

In some embodiments, the optical flux at the input of the U-shaped waveguide 210 is excited by an optical signal source that provides an optical mode matching a transverse mode (e.g., a transverse electric or TE mode) of the U-shaped waveguide 210. For example, in an FDTD simulation, a distributed dipole source may be employed between the input measurement plane $F_{r,in}$ and the PML 240. The distributed dipole source may be configured to produce the matching transverse mode, for example. Further, the distributed dipole source may be configured to provide an optical signal represented by either a sinusoidal wave (i.e., a single frequency) or an impulse (i.e., broadband of frequencies).

In some embodiments when the optical signal is represented by an impulse, a pulse with a fairly broadband Gaussian temporal profile is employed. For optimization of the width and gap size, in some embodiments the pulse may have a frequency spectrum with a center frequency near that of a target frequency (or equivalently a target wavelength) of the optimization. For example, the center frequency may be chosen to be near a resonant frequency of the microring resonator. Further, the pulse spectrum may be broad enough to provide a good chance of finding an eigenmode of the microring resonator, in such embodiments. Further, when modeling 110 the coupled portion, using a pulse essentially allows determination of output coupling ratios $\kappa_{out}$ for a number of different wavelengths simultaneously from a single FDTD simulation.

In some embodiments, the distributed dipole source may be configured to essentially match an unperturbed transverse mode in the waveguide (i.e., in the absence of the microring resonator or other coupling). For example, a Gaussian transverse spatial profile of the distributed dipole source may be chosen that minimizes scattering loss in the waveguide. In another example, a distance between the PML and a measurement plane (e.g., $F_{w,in}$) may be made long enough to allow launching an optical signal from a uniform dipole profile still obtain an essentially lowest-loss mode by the time the optical signal reaches the coupling region.

In some embodiments, selecting 120 the straight waveguide width and the gap size further optimizes a scattering back reflection loss of the U-shaped waveguide and the spaced apart straight waveguide. In some of these embodiments, the scattering back reflection loss is optimized by essentially minimizing a function described by equation (3)

$$\frac{(F2_{w,in} - F1_{w,in})}{F1_{w,in}} \qquad (3)$$

wherein $F2_{w,in}$ is an optical flux measured at an input of the straight waveguide when the input of the straight waveguide is excited by an optical signal and the U-shaped waveguide is present and spaced apart from the straight waveguide by the gap, and wherein $F1_{w,in}$ is an optical flux measured at an input of the straight waveguide when the input of the straight waveguide is excited by an optical signal and the U-shaped waveguide is not present.

For example, referring to FIG. 2, an optical source (e.g., distributed dipole source) may be used to introduce an optical signal at an input of the straight waveguide 220 between the $F_{w,in}$ measurement plane and the PML 240. Then, the optical flux $F2_{w,in}$ is measured as the optical flux at the straight waveguide 220 input measurement plane $F_{w,in}$. In other words, $F2_{w,in}=F_{w,in}$ when the optical source excites an optical mode in the straight waveguide 220 with the U-shaped waveguide 210 being present, as illustrated in FIG. 2.

To measure $F1_{w,in}$, another model that includes only the straight waveguide and no U-shaped waveguide is employed (not illustrated). Using the other model and exciting the straight waveguide at the input end between the $F_{w,in}$ measurement plane and the PML, the optical flux $F1_{w,in}$ is measured as the at the input end of the straight waveguide (e.g., at a measurement plane equivalent to the $F_{w,in}$ measurement plane illustrated in FIG. 2). In other words, $F1_{w,in}$ is essentially an optical flux at the input end of the straight waveguide with the U-shaped waveguide not present. As before, this measurement may be performed using a model of the straight waveguide implemented in an FDTD simulation. Thus, the variables $F2_{w,in}$ and $F1_{w,in}$ both represent measured optical flux at the input of the straight waveguide but for two different simulation configurations with respect to the presence (i.e., $F2_{w,in}$) or absence (i.e., $F1_{w,in}$) of the U-shaped waveguide. Values of the width of the straight waveguide and the gap size for the two configurations above are then selected 120 that minimize equation (2). The selected values are the parameters of a critically coupled optical microring resonator according to some embodiments of the present invention.

Figure 3:
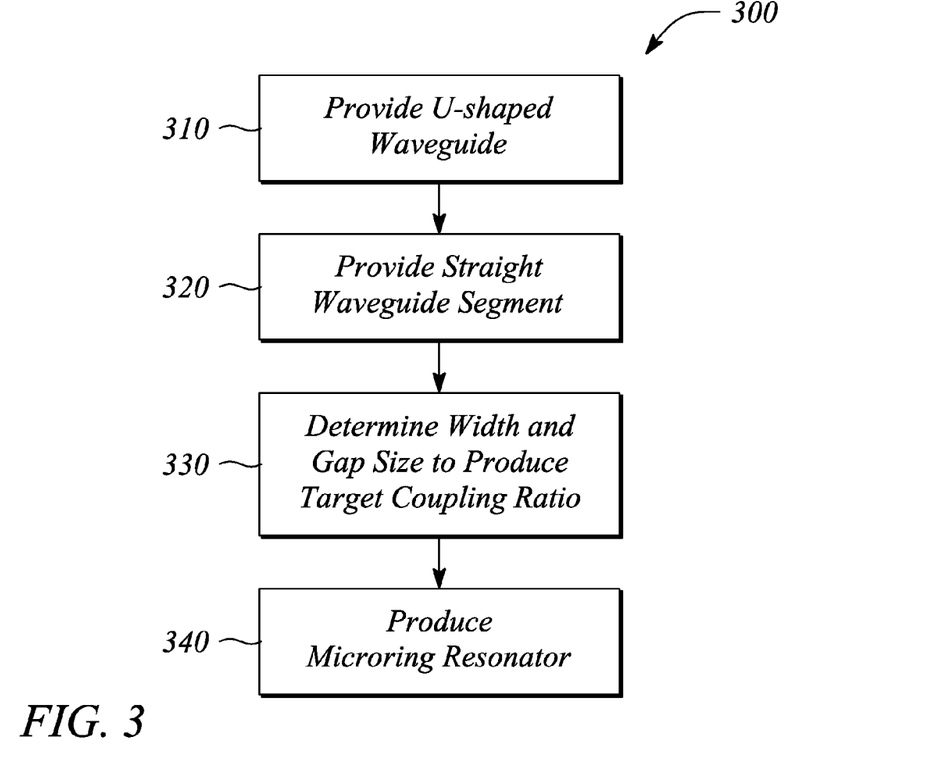
FIG. 3 illustrates a flow chart of a method of producing a microring resonator, according to an embodiment of the present invention.

FIG. 3 illustrates a flow chart of a method 300 of producing a microring resonator, according to an embodiment of the present invention. The method 300 comprises providing 310 a U-shaped waveguide. In some embodiments, the provided 310 U-shaped waveguide may be essentially similar to the U-shaped waveguide described above with respect to the method 100 of determining parameters. For example, the U-shaped waveguide may be provided 310 by constructing the U-shaped waveguide in an FDTD simulation.

The method 300 further comprises providing 320 a straight waveguide segment adjacent to the provided 310 U-shaped waveguide. The provided 320 straight waveguide segment is spaced apart from the U-shaped waveguide by a gap. The provided 320 straight waveguide segment may be essentially similar to the straight waveguide described above with respect to the method 100 of determining parameters.

For example, the U-shaped waveguide and straight waveguide segment may be provided 310, 320 by constructing models of respective ones of the U-shaped waveguide and straight waveguide segment in an FDTD simulation. In another embodiment, the U-shaped waveguide and straight waveguide segment may be provided 310, 320 by fabricating actual models using semiconductor fabrication, for example.

The method 300 of producing further comprises determining 330 values of a width of the straight waveguide segment and a size of the gap that produces a target output coupling ratio. In some embodiments, determining 330 values comprises optimizing the straight waveguide segment width and the gap size to produce the target output coupling ratio. For example, determining 330 values may employ multiple FDTD simulations of the U-shaped waveguide and the straight waveguide segment using different widths and gap sizes and selecting a combination of the width and gap size that best achieves the target output coupling ratio.

In some embodiments, the target output coupling ratio is given by a ratio of an optical flux at an output of the straight waveguide segment to an optical flux at an input of the U-shaped waveguide when the input of the U-shaped waveguide is excited by an optical signal that essentially matches a transverse mode of the U-shaped waveguide. The output coupling ratio may be essentially similar to the output coupling ratio $\kappa_{out}$ given by equation (2) above, for example.

In some embodiments, determining 330 values of a width of the straight waveguide segment and a size of the gap further optimizes a scattering back reflection loss in the straight waveguide segment in the presence of the U-shaped waveguide. In some embodiments, the scattering back reflection loss is optimized by essentially minimizing the function described by equation (3), above. For example, determining 330 values may employ multiple FDTD simulations of the U-shaped waveguide and the straight waveguide segment using different widths and gap sizes and selecting a combination of the width and gap size that best achieves the target output coupling ratio and essentially minimizes the scattering back reflection loss as represented minimizing equation (3).

The method 300 of producing further comprises producing 340 a microring resonator comprising a ring-shaped waveguide adjacent to a bus waveguide using the determined value of the straight waveguide segment width as a width of the bus waveguide and the determined gap size as a spacing between the microring and the bus waveguide. In some embodiments, a width of a waveguide of the microring is determined by a width of the U-shaped waveguide. In some embodiments, the straight waveguide segment width is less than the U-shaped waveguide width and the gap size is greater than the straight waveguide width. For example, producing 340 a microring resonator may comprise forming the microring waveguide and the bus waveguide in a surface of a silicon on insulator substrate. The determined gap size may be greater than about 300 nm and the bus waveguide width may be between 250 nm and 300 nm, for example.

In some embodiments (not illustrated), the method of producing a microring resonator further comprises selecting the width of the U-shaped waveguide to achieve a target value of an unloaded quality factor (Q) of the microring resonator. The selection of the U-shaped waveguide width is performed prior to determining 330 a value of a width of the straight waveguide segment and a size of the gap. For the example above, the microring waveguide width may be selected to be about 450 nm and have a radius of about 1.33 μm. Further, an operational wavelength of the microring resonator may be about 1.55 μm, for example.

Figure 4:
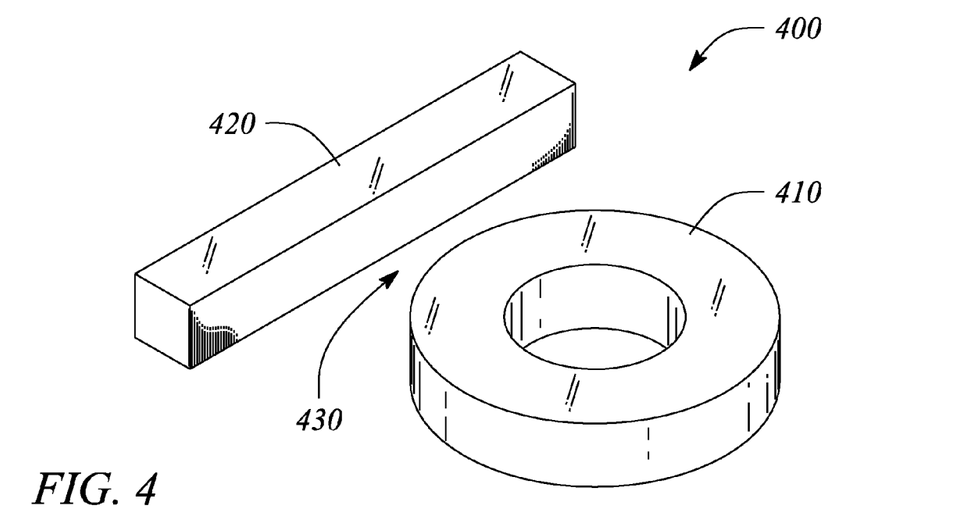
FIG. 4 illustrates a perspective view of a critically coupled microring resonator, according to an embodiment of the present invention.

FIG. 4 illustrates a perspective view of a critically coupled microring resonator 400, according to an embodiment of the present invention. In particular, the critically coupled microring resonator 400 may be formed in or on a surface of a substrate. For example, the substrate may comprise a silicon on insulator (SOI) substrate and waveguides of the microring resonator 400 may comprise ridge waveguides formed in a top silicon layer of the SOI substrate. The ridge waveguides may be formed by etching or equivalent semiconductor fabrication methods, for example.

The critically coupled microring resonator 400 comprises a microring waveguide 410 having a radius that is less than about 2 microns. The critically coupled microring resonator 400 further comprises a straight waveguide adjacent to but spaced apart from the microring waveguide 410. The straight waveguide 420 has a width and is spaced apart from the microring waveguide 420 by a gap 430. In some embodiments, a ratio of the width of the straight waveguide 420 to the width of the microring waveguide 410 is less than about 0.7. In some embodiments, a ratio of a size of the gap 430 to the microring waveguide 410 width is greater than about 0.5. For example, the width of the microring waveguide 410 may be about 450 nm, the straight waveguide width is between 250 nm and 300 nm and the gap size is greater than about 300 nm.

In some embodiments, the microring waveguide width is determined by a target unloaded quality factor Q of the microring resonator. In some embodiments, the microring waveguide 410 and the straight waveguide 420 comprise ridge waveguides having a ridge height of about 250 nm. In some embodiments, the ridge waveguides are fabricated on a substrate comprising silicon (e.g., a silicon on insulator substrate), as mentioned above. In some embodiments, the straight waveguide 420 width and gap size of the gap 430 are selected to simultaneously optimize an output coupling ratio and a scattering back reflection loss in the straight waveguide of the microring resonator.

Thus, there have been described embodiments of a microring resonator, a method of determining parameters of and a method of producing a microring resonator that critically couple the microring resonator to a bus waveguide. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. A method of determining parameters of a critically coupled optical microring resonator, the method comprising:
    modeling a coupled portion of the microring resonator as a U-shaped waveguide spaced apart from a straight waveguide by a gap, the U-shaped waveguide having a width that is equivalent to a width of a waveguide of the microring resonator and the microring resonator having a radius that is less than about 2 microns;
    selecting a width of the straight waveguide and a size of the gap to optimize an output coupling ratio between the U-shaped waveguide and the straight waveguide;
    wherein the selected straight waveguide width and the selected gap size are the determined parameters of the critically coupled optical microring resonator, and wherein a ratio of the selected straight waveguide width to the microring waveguide width is less than about 0.7 and a ratio of the selected gap size to the microring waveguide width is greater than about 0.5.

2. The method of determining parameters of claim 1, wherein modeling comprises providing a finite difference time domain (FDTD) model of the U-shaped waveguide and the straight waveguide, ends of the U-shaped waveguide and ends of the straight waveguide each being terminated in a matched boundary layer of the FDTD model.

3. The method of determining parameters of claim 2, wherein the FDTD model is a three dimensional (3D) FDTD model, and wherein the matched boundary layer is a perfectly matched layer.

4. The method of determining parameters of claim 1, wherein the output coupling ratio is given by a ratio of an optical flux measured at an output of the straight waveguide to an optical flux measured at an input of the U-shaped waveguide, the input of the U-shaped waveguide being excited by an optical signal that matches a transverse mode of the U-shaped waveguide.

5. The method of determining parameters of claim 1, wherein selecting the straight waveguide width and the gap size further optimizes a scattering back reflection loss of the U-shaped waveguide and the straight waveguide.

6. The method of determining parameters of claim 5, wherein the scattering back reflection loss is optimized by essentially minimizing a relation:

$$\frac{(F2_{w,in} - F1_{w,in})}{F1_{w,in}}$$

wherein $F2_{w,in}$ is an optical flux measured at an input of the straight waveguide when the input of the straight waveguide is excited by an optical signal and the U-shaped waveguide is both present and spaced apart from the straight waveguide by the gap, and wherein $F1_{w,in}$ is an optical flux measured at an input of the straight waveguide when the input of the straight waveguide is excited by an optical signal and the U-shaped waveguide is not present.

7. The method of determining parameters of claim 1, wherein the selected straight waveguide width is less than the U-shaped waveguide width, and wherein the selected gap size is greater than the straight waveguide width.

8. The method of determining parameters of claim 1, wherein the U-shaped waveguide comprises a semi-circular waveguide segment and a pair of straight waveguide segments, a first straight waveguide segment of the pair being connected to a first end of the semi-circular waveguide segment and a second straight waveguide segment being connected a second end of the semi-circular waveguide segment, the semi-circular waveguide segment having a radius that is equivalent to a radius of the coupled portion of the microring resonator being modeled.

9. A method of producing a microring resonator, the method comprising:
providing a U-shaped waveguide;
providing a straight waveguide segment adjacent to the U-shaped waveguide, the straight waveguide segment being spaced apart from the U-shaped waveguide by a gap;
determining a value of a width of the straight waveguide segment and a size of the gap that produces a target output coupling ratio; and
producing a microring resonator having a radius less than about 2 microns that comprises a ring-shaped waveguide adjacent to a bus waveguide, wherein producing comprises using the determined value of the straight waveguide segment width as a width of the bus waveguide and using the determined gap size as a spacing between the ring-shaped waveguide and the bus waveguide, a width of the ring-shaped waveguide being determined by a width of the U-shaped waveguide,
wherein a ratio of the bus waveguide width to the ring-shaped waveguide width is less than about 0.7 and a ratio of the determined gap size to the ring-shaped waveguide width is greater than about 0.5.

10. The method of producing a microring resonator of claim 9, wherein the target output coupling ratio is given by a ratio of an optical flux at an output of the straight waveguide segment to an optical flux at an input of the U-shaped waveguide, the input of the U-shaped waveguide being excited by an optical signal that essentially matches a transverse mode of the U-shaped waveguide.

11. The method of producing a microring resonator of claim 9, further comprising selecting the width of the U-shaped waveguide to achieve a target value of an unloaded quality factor (Q) of the microring resonator, wherein selecting the U-shaped waveguide width is performed prior to determining a value of a width of the straight waveguide segment and a size of the gap.

12. The method of producing a microring resonator of claim 9, wherein determining a value of a width of the straight waveguide segment and a size of the gap optimizes a scattering back reflection loss in the straight waveguide segment in the presence of the U-shaped waveguide, the scattering back reflection loss being optimized by essentially minimizing a function given by $$\frac{(F2_{w,in} - F1_{w,in})}{F1_{w,in}}$$

wherein $F2_{w,in}$ is an optical flux measured at an input of the straight waveguide when the input of the straight waveguide is excited by an optical signal and the U-shaped waveguide is both present and spaced apart from the straight waveguide by the gap, and wherein $F1_{w,in}$ is an optical flux measured at an input of the straight waveguide when the input of the straight waveguide is excited by an optical signal and the U-shaped waveguide is not present.

13. The method of producing a microring resonator of claim 9, wherein the U-shaped waveguide and the straight waveguide are provided by constructing a finite difference time domain (FDTD) model of the U-shaped waveguide and the straight waveguide segment, ends of the U-shaped waveguide and ends of the straight waveguide segment each being terminated in a matched boundary layer of the FDTD model.

14. The method of producing a microring resonator of claim 9, wherein the straight waveguide segment width is less than the U-shaped waveguide width, and wherein the gap size is greater than the straight waveguide width.

15. The method of producing a microring resonator of claim 14, wherein producing a microring resonator comprises forming both the ring-shaped waveguide and the bus waveguide in a surface of a silicon on insulator substrate, the determined gap size being greater than about 300 nanometers, the bus waveguide width being between 250 nanometers and 300 nanometers.

16. A critically coupled optical microring resonator comprising:
- a microring waveguide having a radius that is less than about 2 microns;
- a straight waveguide adjacent to but spaced apart from the microring waveguide, the straight waveguide having a width and being spaced apart from the microring waveguide by a gap,
- wherein a ratio of the straight waveguide width to a width of the microring waveguide is less than about 0.7, and wherein a ratio of a size of the gap to the microring waveguide width is greater than about 0.5.

17. The critically coupled optical microring resonator of claim 16, wherein the width of the microring waveguide is about 450 nanometers, the straight waveguide width being between 250 nanometers and 300 nanometers, and the gap size being greater than about 300 nanometers.

18. The critically coupled optical microring resonator of claim 16, wherein the microring waveguide width is determined by a target unloaded quality factor Q of the microring resonator.

19. The critically coupled optical microring resonator of claim 16, wherein the microring waveguide and the straight waveguide each comprises a ridge waveguide having a ridge height of about 250 nanometers, the ridge waveguide comprising silicon.

20. The critically coupled optical microring resonator of claim 16, wherein the straight waveguide width and the gap size are selected to simultaneously optimize an output coupling ratio and a scattering back reflection loss in the straight waveguide of the microring resonator.

* * * * *